United States Patent [19]

Moretz et al.

[11] Patent Number: 5,297,296
[45] Date of Patent: * Mar. 29, 1994

[54] MULTI-LAYER MOISTURE MANAGEMENT ELASTIC FABRIC

[76] Inventors: Herbert L. Moretz, 20205 Lola Cir., Davidson, N.C. 28036; Daniel L. Brier, 33 Angelfish Cay Dr., Key Largo, Fla. 33037

[*] Notice: The portion of the term of this patent subsequent to Dec. 14, 2010 has been disclaimed.

[21] Appl. No.: 991,761

[22] Filed: Dec. 17, 1992

Related U.S. Application Data

[63] Continuation-in-part of Ser. No. 945,677, Sep. 16, 1992, which is a continuation-in-part of Ser. No. 842,224, Feb. 26, 1992, Pat. No. 5,210,882, which is a continuation-in-part of Ser. No. 791,066, Nov. 12, 1991, Pat. No. 5,217,782.

[51] Int. Cl.$^5$ ............... A41D 20/00; A41D 27/00
[52] U.S. Cl. ............................... 2/237; 2/400; 2/170; 2/171.8; 2/181; 2/174; 2/243.1; 2/DIG. 11; 66/177; 604/358; 602/76; 602/58; 602/44; 602/75
[58] Field of Search ............. 2/400, 403, 406, 170, 2/171.8, 181, 174, 401, 237, DIG. 11, DIG. 7, 243 R, 243 A, 243.1; 66/169 R, 170, 172 E, 202, 185, 177; 428/238, 253; 604/358; 602/76, 58, 44, 75

[56] References Cited

U.S. PATENT DOCUMENTS

| | | | |
|---|---|---|---|
| 3,570,482 | 3/1971 | Emoto | 602/76 |
| 3,887,968 | 6/1975 | Lynam | 24/266 |
| 4,236,550 | 12/1980 | Braun et al. | 602/76 |
| 4,244,199 | 1/1981 | Rhode | 66/193 |
| 4,338,371 | 7/1982 | Dawn et al. | 428/283 |
| 4,341,096 | 7/1982 | Safrit et al. | 66/185 |
| 4,422,307 | 12/1983 | Thorneburg | 66/202 |
| 4,502,156 | 3/1985 | Wishman | 2/181 |
| 4,520,635 | 6/1985 | Shields et al. | 66/185 |
| 4,761,324 | 8/1988 | Rautenberg | 428/190 |
| 4,916,005 | 4/1990 | Lippert et al. | 428/192 |
| 4,941,933 | 7/1990 | Korpman | 156/160 |
| 5,133,199 | 7/1992 | Parikh et al. | 602/76 |

Primary Examiner—Clifford D. Crowder
Assistant Examiner—Gloria Hale
Attorney, Agent, or Firm—W. Thad Adams, III

[57] ABSTRACT

A multi-layer moisture management elastic fabric including a moisture transport fabric layer constructed of hydrophobic yarns and defining a first fabric face for residing in skin contact during garment wear and for wicking moisture away from the skin. A moisture dispersal fabric layer is constructed of hydrophilic yarns and defines a second fabric face for residing in spaced-apart relation from the skin during garment wear and for receiving moisture from the hydrophobic moisture transport layer. Elastic yarns are integrated with the yarns of the moisture transport fabric layer and the yarns of the moisture dispersal fabric layer to form a single, integrated fabric which is highly elastic. The fabric is useful as waistband material and as athletic headbands, wristbands and as medical bandages and braces.

19 Claims, 11 Drawing Sheets

MULTI-LAYER MOISTURE MANAGEMENT ELASTIC FABRIC

TECHNICAL FIELD AND BACKGROUND OF THE INVENTION

This application is a continuation-in-part of application Ser. No. 945,677, filed on Sep. 16, 1992 which is a continuation-in-part of Ser. No. 842,224, now U.S. Pat. No. 5,210,882 filed on Feb. 26, 1992, which is a continuation-in-part of application Ser. No. 791,066, now U.S. Pat. No. 5,217,782 filed on Nov. 12, 1991.

This invention relates to garments, including but not limited to, garments which are constructed from a moisture management fabric of the type disclosed and claimed in prior-filed applications referred to above. As used in this application, the term "moisture management" may refer to the management of urine discharged into the garment by mild to moderately incontinent wearers, or to perspiration resulting from work, athletic activity or any other activity.

Examples of such garments are mens' boxer shorts and briefs, athletic apparel such as sweat pants, running shorts, athletic supporters, uniforms, pajamas, bathing suits, and womens' panties, brassieres and similar undergarments, as well as medical bandages and braces, head, wrist hat and arm bands, and the like.

The fabric from which these moisture management garments are constructed is intended to quickly move moisture away from the skin of the wearer and slow the outward movement of the moisture while at the same time enhancing the dispersion of the moisture to those fibers of the fabric which do not touch the skin. The fabric also permits gradual migration of moisture in the form of vapor to the outer surface of the fabric in a controlled manner where evaporation will occur. The result of these functions is to keep the skin as dry as possible while preventing outer clothing from becoming wet from urine or perspiration through the undergarment from inside to outside. This prevents urine or perspiration-soaked garments from residing next to the skin over a period of time. This condition can cause odor, chafing, irritation and conditions conducive to bacteria, fungus and yeast growth.

A number of problems must be solved to provide a fabric which truly manages moisture in an efficient and hygienic manner, and to incorporate that fabric into a suitable garment. Such a fabric should also take advantage of the inherent shape of the garment by moving moisture to those areas where dispersion and evaporation can most readily be accomplished, and where penetration of moisture through to the other areas of the garment and to outer clothing is minimized. In general, this involves, as disclosed herein for certain garments, moving the moisture upwardly towards the waist and away from the crotch area. The waist area has a much greater surface area than the crotch and therefore can accommodate the spreading liquid over a much larger area. Of course, the problem to be solved is how to get the moisture to move upwardly against the pull of gravity. Prior applications addressed the solution to this problem. This application addresses the problem of how to prevent the moisture, once it has migrated upwardly towards the waist, from soaking into the elastic waistband of such garments and remaining in contact with the skin under the waistband, and the related problems associated with medical body wraps and athletic sweatbands.

SUMMARY OF THE INVENTION

Therefore, it is an object of the invention to provide a moisture management garment such as an undergarment which has portions such as a waistband which are constructed from an integral multi-layer fabric which has moisture management characteristics.

It is another object of the invention to provide a moisture management fabric which can be easily fabricated without extensive labor by producing the fabric in a single step on a textile processing machine.

It is another object of the invention to provide a moisture management fabric which can be incorporated into the waistband, leg opening or similar area of garments, such as undergarments, pajamas, athletic apparel and the like.

It is another object of the invention to provide a waistband which wicks moisture away from an adjacent body surface.

It is another object of the invention to provide a moisture management fabric which is constructed of an integral multi-layer fabric which has adjacent layers of hydrophobic and hydrophilic fabrics which exert a simultaneous push-pull effect on moisture to thereby move the moisture from one side of the adjacent layers to the other side.

It is another object of the invention to provide a moisture-management garment constructed of a integral multi-layer fabric which incorporates one or more layers which are highly elastic.

It is another object of the invention to provide a brassiere which includes components constructed of a moisture management fabric according to the present invention;

These and other objects of the present invention are achieved in the preferred embodiments disclosed below by providing a multi-layer moisture management elastic fabric, comprising a moisture transport fabric layer constructed of hydrophobic yarns and defining a first fabric face for residing in skin contact during garment wear and for wicking moisture away from the skin. A moisture dispersal fabric layer is constructed of hydrophilic yarns and defines a second fabric face for residing in spaced-apart relation from the skin during garment wear and for receiving moisture from the hydrophobic moisture transport layer. Elastic yarns are integrated with the yarns of the moisture transport fabric layer and the yarns of the moisture dispersal fabric layer to form a single, integrated fabric which is highly elastic.

According to one preferred embodiment of the invention, the hydrophobic yarns and the hydrophilic yarns of the elastic fabric are warp knitted. The elastic yarns are laid into the structure of the warp knitted yarns.

According to another preferred embodiment of the invention, the hydrophobic yarn of the moisture transport layer is chosen from the group consisting of polyester and polypropylene.

According to yet another preferred embodiment of the invention, the hydrophilic yarn of the moisture dispersal fabric layer is chosen from the group consisting of hydrophilic nylon, cotton and rayon.

According to yet another preferred embodiment of the invention, the elastic yarn is chosen from the group consisting of rubber, latex and a long chain polyurethane elastomer.

According to another preferred embodiment of the invention, the structure of the warp knitting is a Raschel structure.

According to yet another preferred embodiment of the invention, the fabric comprises a narrow-width elastic fabric having stretch of no less than 100 percent in the lengthwise direction and substantially no stretch in the width direction.

According to yet another preferred embodiment of the invention, the elastic fabric comprises a waistband for a garment.

According to yet another preferred embodiment of the invention, the elastic fabric comprises a body part support wrap.

According to yet another preferred embodiment of the invention, the elastic yarns are laid into the fabric intermediate the moisture transport fabric layer and the moisture dispersal fabric layer.

According to one preferred embodiment of the invention, a warp-knitted multi-layer moisture management elastic fabric is provided, and comprises a moisture transport fabric layer constructed of hydrophobic yarns and defining a knitted first fabric face for residing in skin contact during garment wear and for wicking moisture away from the skin. A moisture dispersal fabric layer is integrated by knitting with the moisture transport fabric layer. The moisture dispersal fabric layer is constructed of hydrophilic yarns and defines a knitted second fabric face obverse to the first fabric face for residing in spaced-apart relation from the skin during garment wear and for receiving moisture from the hydrophobic moisture transport layer. Elastic yarns are integrated by being laid in with the yarns of the moisture transport fabric layer and the yarns of the moisture dispersal fabric layer to form a single, integrated fabric which is highly elastic. The elastic fabric comprises a narrow-width elastic fabric having stretch of no less than 100 percent in the lengthwise direction and substantially no stretch in the width direction.

According to another preferred embodiment of the invention, the fabric is no less than one inch wide and no more than two inches wide.

According to yet another preferred embodiment of the invention, the hydrophobic yarns and the hydrophilic yarns of the elastic fabric are warp knitted, and the elastic yarns are laid into the structure of the warp knitted yarns.

According to yet another preferred embodiment of the invention, the hydrophobic yarn of the moisture transport layer is chosen from the group consisting of polyester and polypropylene.

According to yet another preferred embodiment of the invention, the hydrophilic yarn of the moisture dispersal fabric layer is chosen from the group consisting of hydrophilic nylon, cotton and rayon.

According to yet another preferred embodiment of the invention, the elastic yarn is chosen from the group consisting of rubber, latex and a long chain polyurethane elastomer.

According to yet another preferred embodiment of the invention, the structure of the warp knitting is a Raschel structure.

According to yet another preferred embodiment of the invention, the fabric is combined with a garment to form the waistband of the garment.

According to yet another preferred embodiment of the invention, the fabric is formed into a body wrap.

According to yet another preferred embodiment of the invention, the fabric is formed into components of a brassiere.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
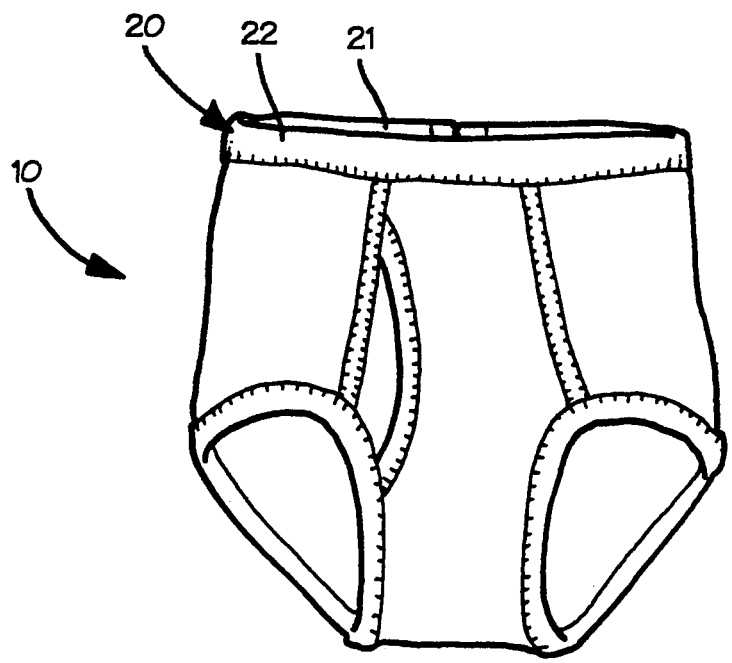
FIG. 1 is garment including an elastic moisture managing waistband according to an embodiment of the present invention.

Referring now specifically to the drawings, a moisture management garment incorporating an elastic moisture management fabric according to a preferred embodiment of the invention is shown in FIGS. 1 (front view) and 2 (rear view), and broadly indicated at reference numeral 10. The garment 10 is shown as a pair of men's briefs, but can be any elastic-waisted garment such as pajamas, underwear, athletic wear, infant wear or any other apparel, such as apparel with elastic leg openings or straps, with which a moisture management elastic waistband would be useful. For purposes of example, the garment 10 may be a moisture management garment of the type disclosed in applicant's prior applications, noted above.

Whatever the garment 10, a waistband 20 according to the invention is sewn, for example, by overedge seaming stitches, to the top of the garment 10 in a conventional manner.

Figure 3:
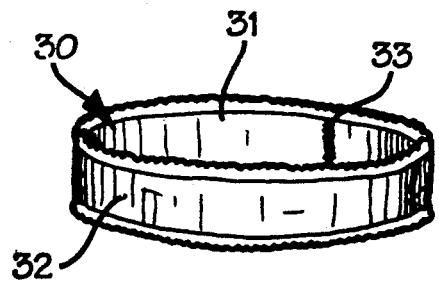
FIG. 3 is a headband made from the elastic moisture management garment according to an embodiment of the invention.
Figure 4:
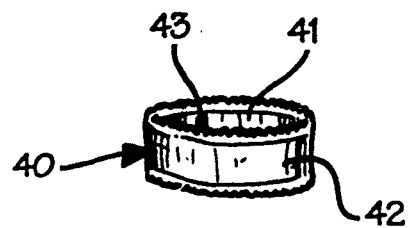
FIG. 4 is a wristband made from the elastic moisture management garment according to an embodiment of the invention.
Figure 5:
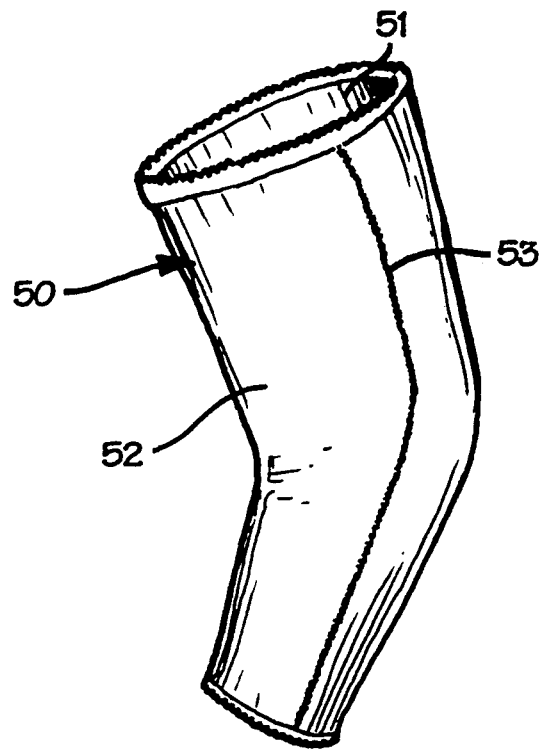
FIG. 5 is a elbow or knee brace made from the elastic moisture management garment according to an embodiment of the invention.
Figure 6:
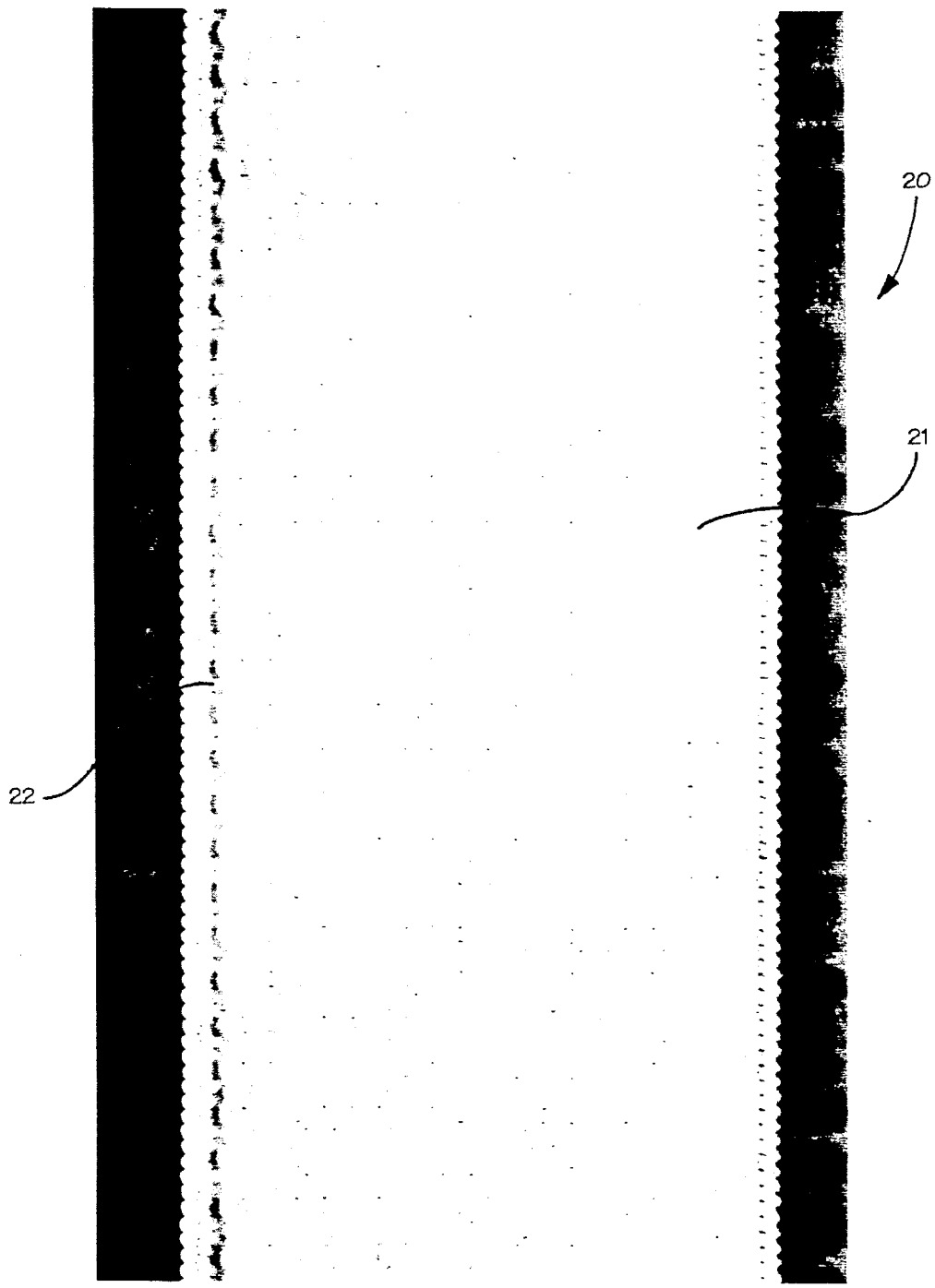
FIG. 6 is a view of the inner, hydrophobic side of the elastic moisture management fabric according to a preferred embodiment of the invention.
Figure 7:
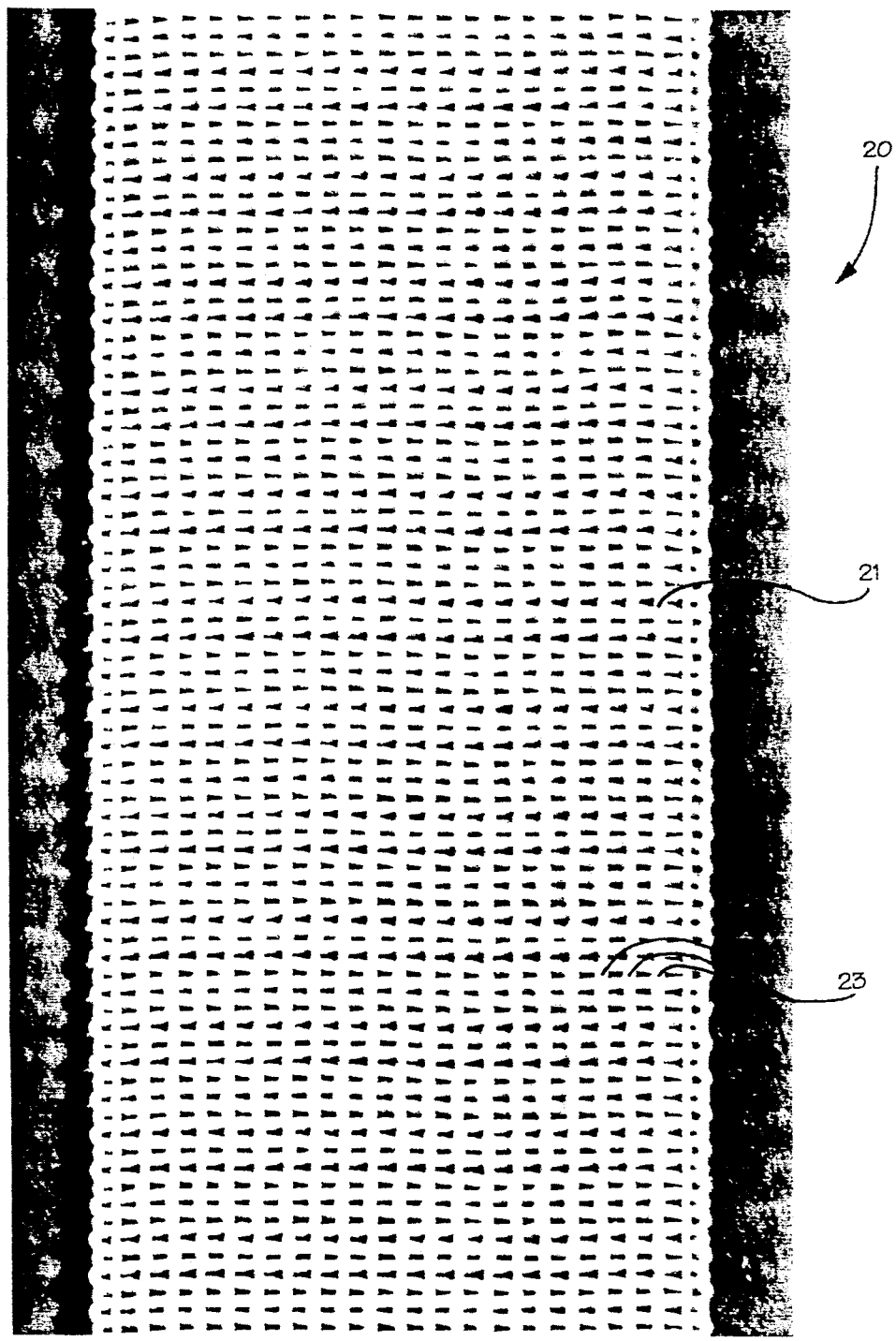
FIG. 7 is a view of the inner, hydrophobic side of the elastic moisture management fabric in a stretched condition to show more clearly the knitted structure of the fabric.
Figure 8:
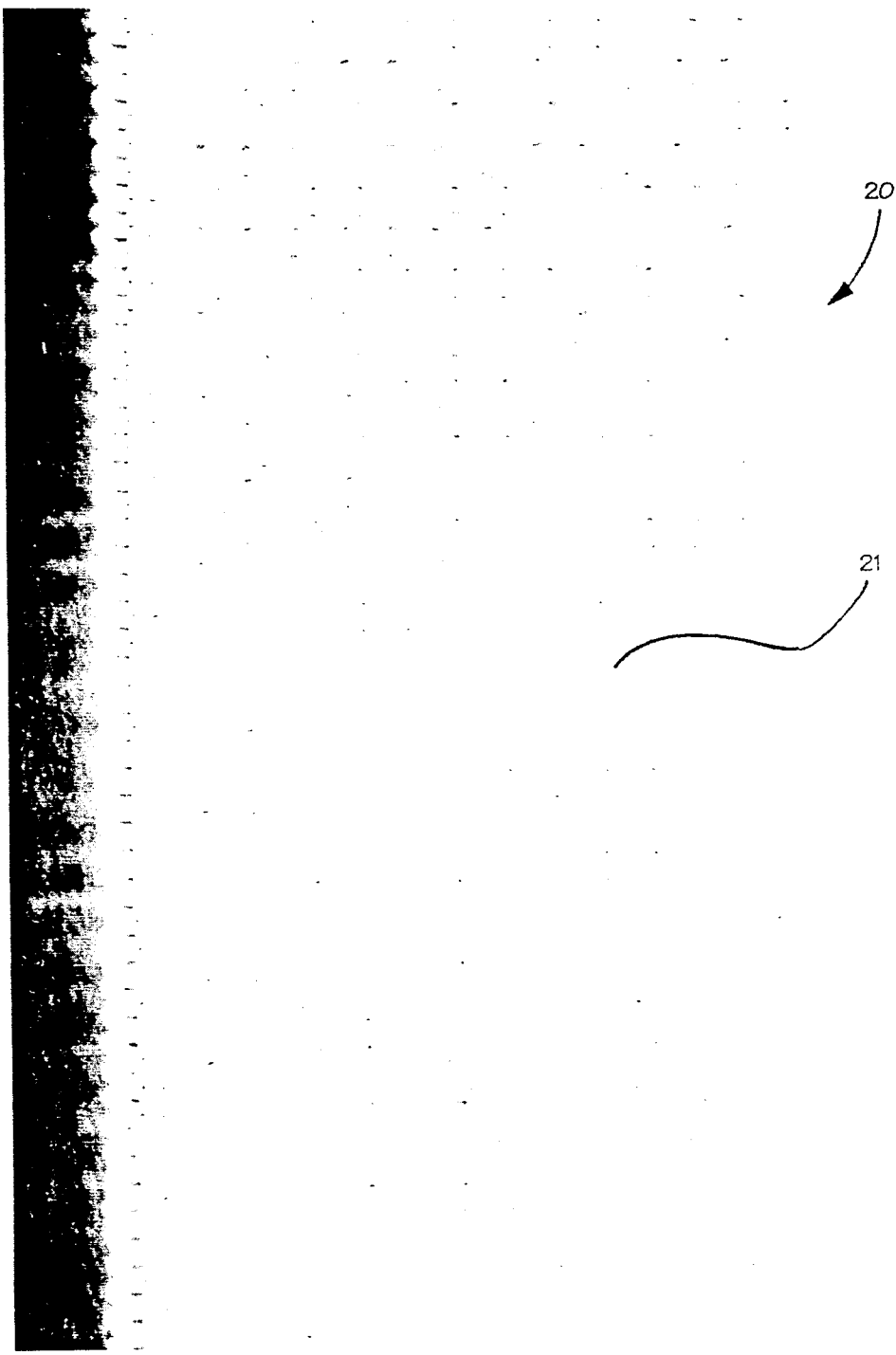
FIG. 8 is an enlarged view of the inner, hydrophobic side of the elastic moisture management fabric in a relaxed condition.
Figure 9:
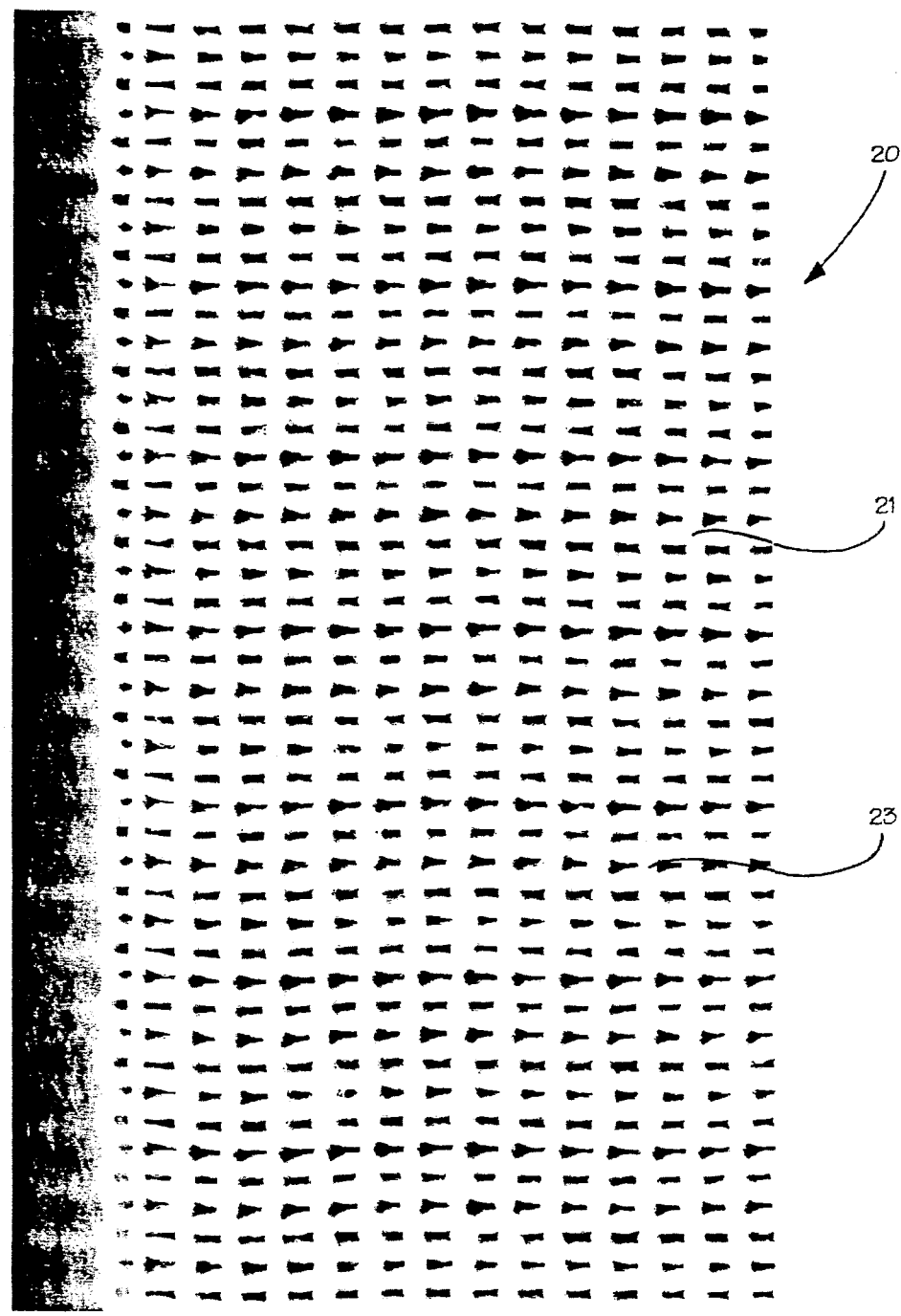
FIG. 9 is an enlarged view of the inner, hydrophobic side of the elastic moisture management fabric in a stretched condition.
Figure 10:
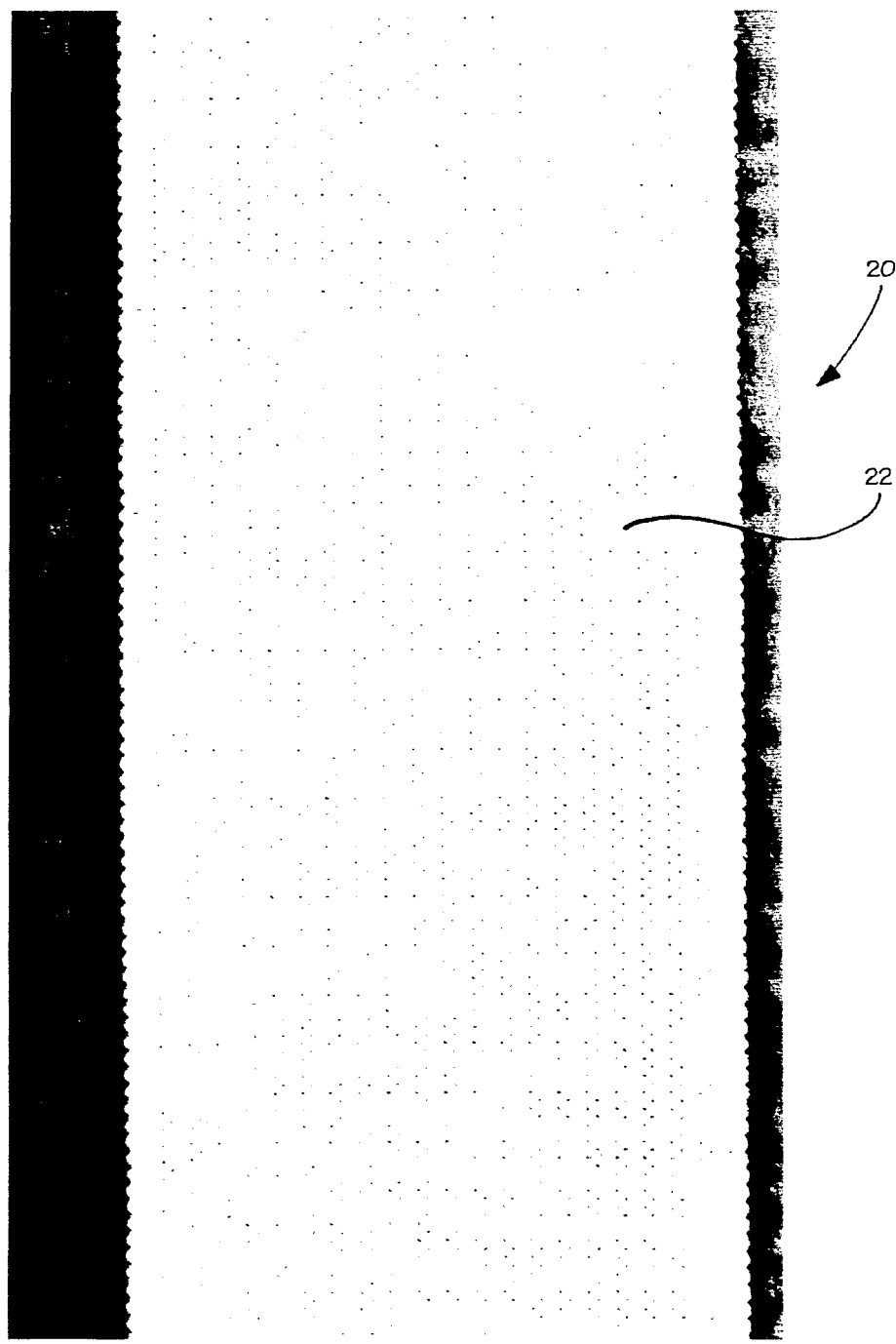
FIG. 10 is a view of the outer, hydrophilic side of the elastic moisture management fabric according to a preferred embodiment of the invention.
Figure 11:
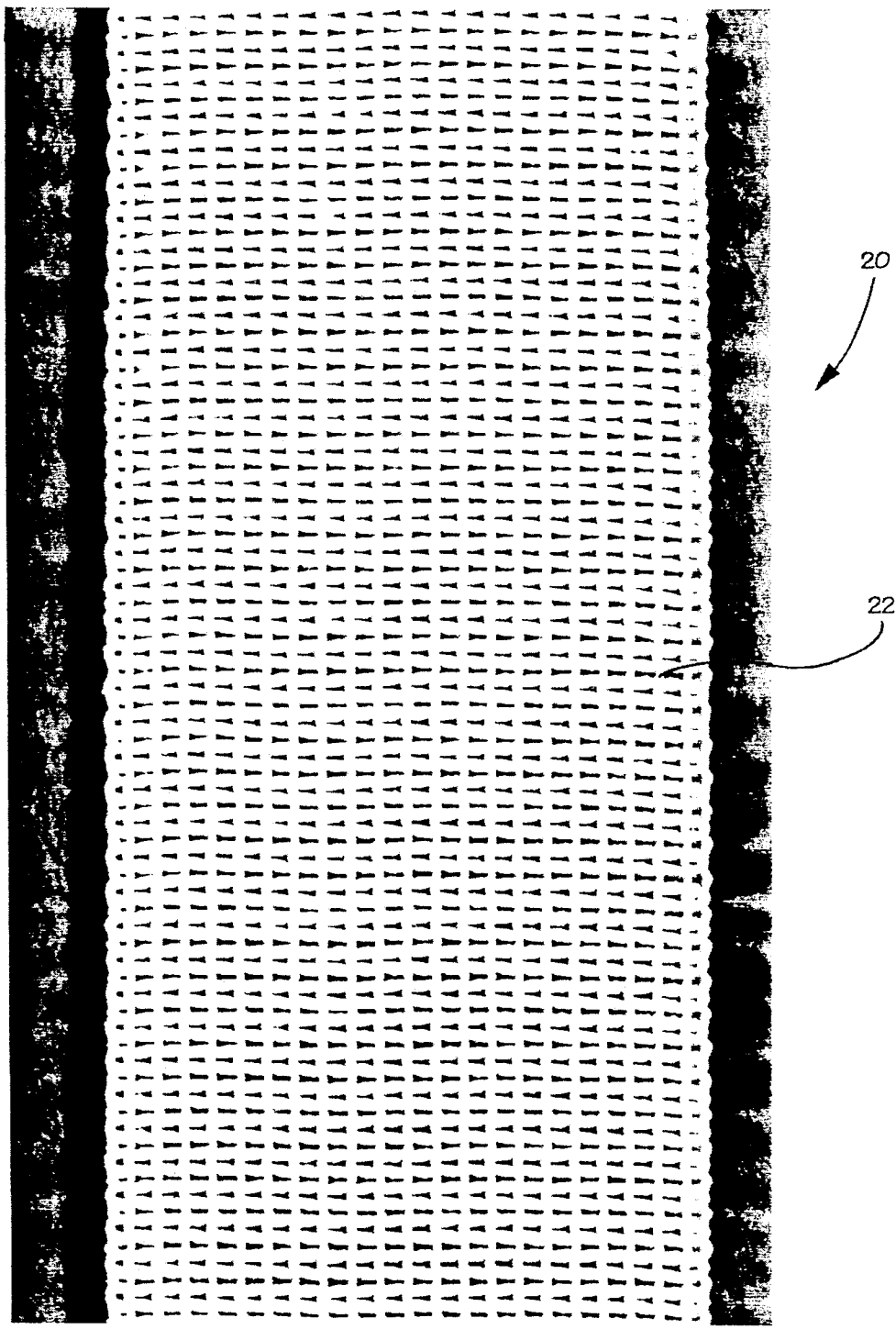
FIG. 11 is a view of the outer, hydrophilic side of the elastic moisture management fabric in a stretched condition to show more clearly the knitted structure of the fabric.
Figure 12:
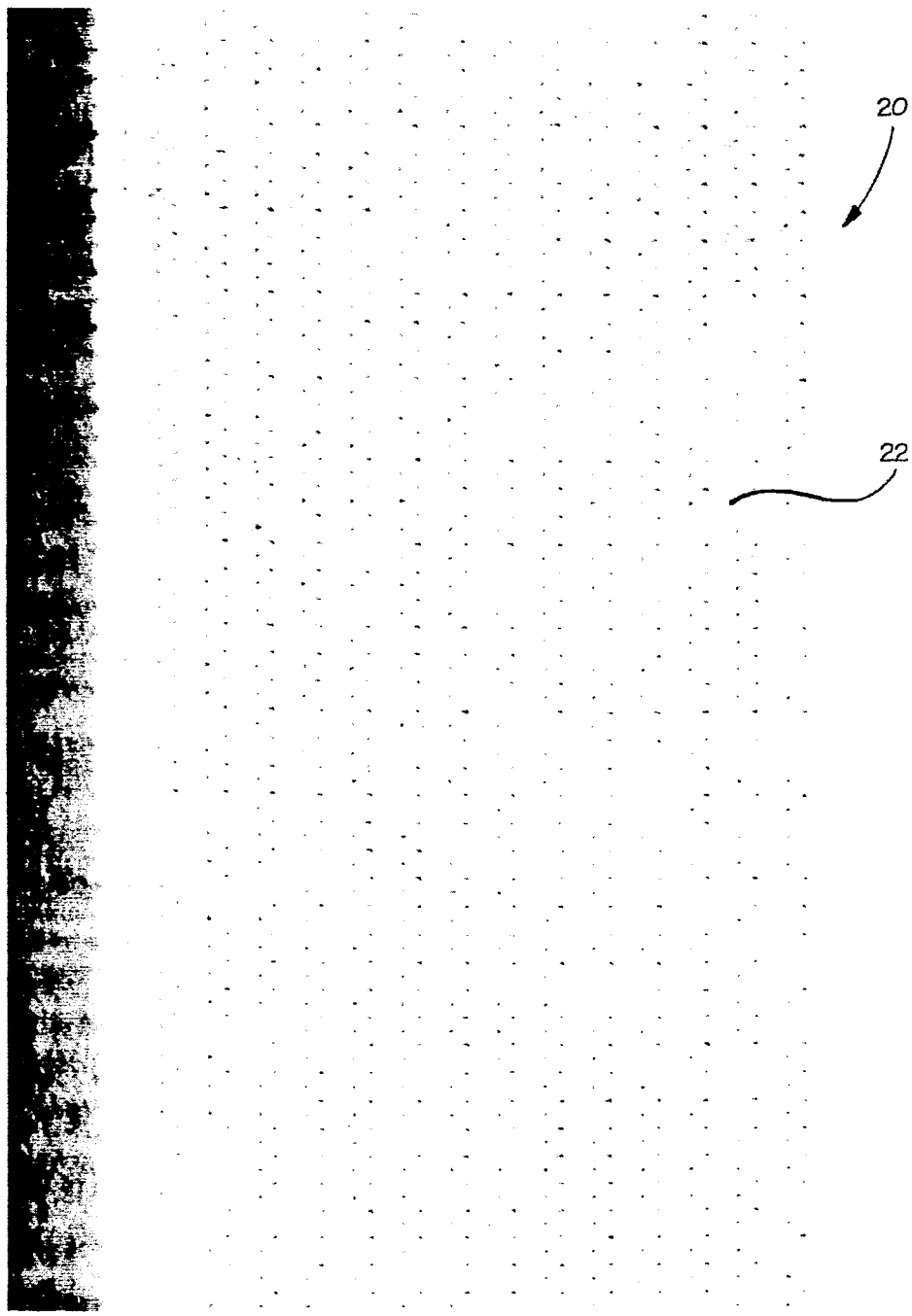
FIG. 12 is an enlarged view of the outer, hydrophilic side of the elastic moisture management fabric in a relaxed condition.
Figure 13:
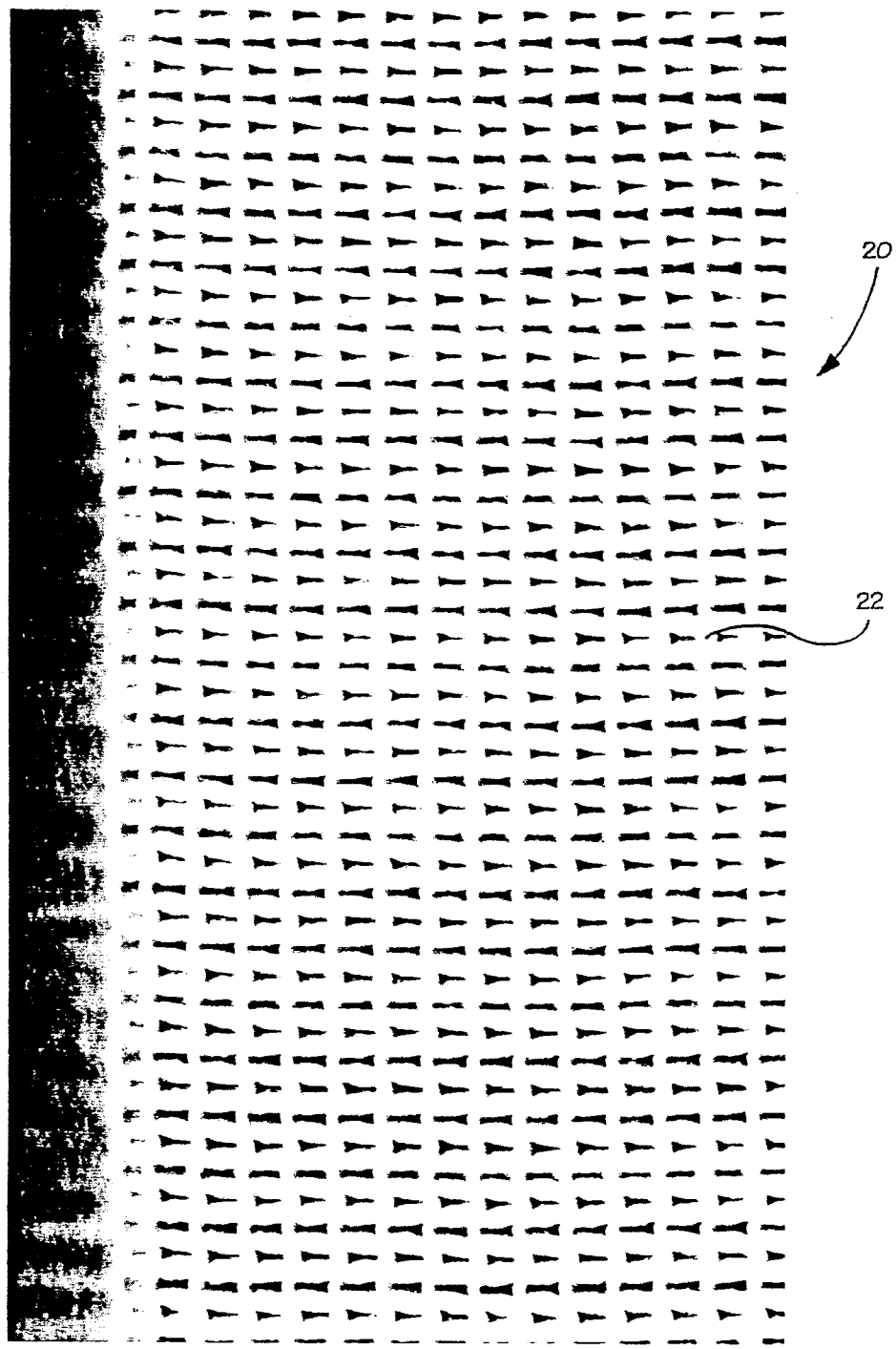
FIG. 13 is an enlarged view of the outer, hydrophilic side of the elastic moisture management fabric in a stretched condition.

FIGS. 3, 4 and 5 illustrate other embodiments of the moisture management elastic fabric claimed in this application. In accordance with the disclosure of this application, a headband 30 suitable for athletic use is shown in FIG. 3. The headband 30 is constructed of a relatively narrow moisture management elastic fabric according to the disclosure of this application. Hydrophobic inner yarns 31 and hydrophilic outer yarns 32 provide moisture management, as described below.

A wristband 40 suitable for athletic use is shown in FIG. 4. The headband 40 is constructed of a relatively wider moisture management elastic fabric according to the disclosure of this application. Hydrophobic inner yarns 41 and hydrophilic outer yarns 42 provide moisture management, as described below.

The headband 30 and wristband 40 may also include additional absorbent yarns, such as cotton terry yarns, for additional absorbency. Ordinarily these additional yarns would be placed on the outer surface of the item where the moisture thus absorbed may be more easily evaporated. The elastic yarns are selected as to number, spacing and degree of stretch to suit the needs of the particular item.

A knee or elbow brace 50 suitable for medical use is shown in FIG. 5. The knee or elbow brace 50 is constructed of a relatively wide moisture management elastic fabric according to the disclosure of this application, with relatively numerous and strong elastic yarns to provide substantial support.

Figure 14:
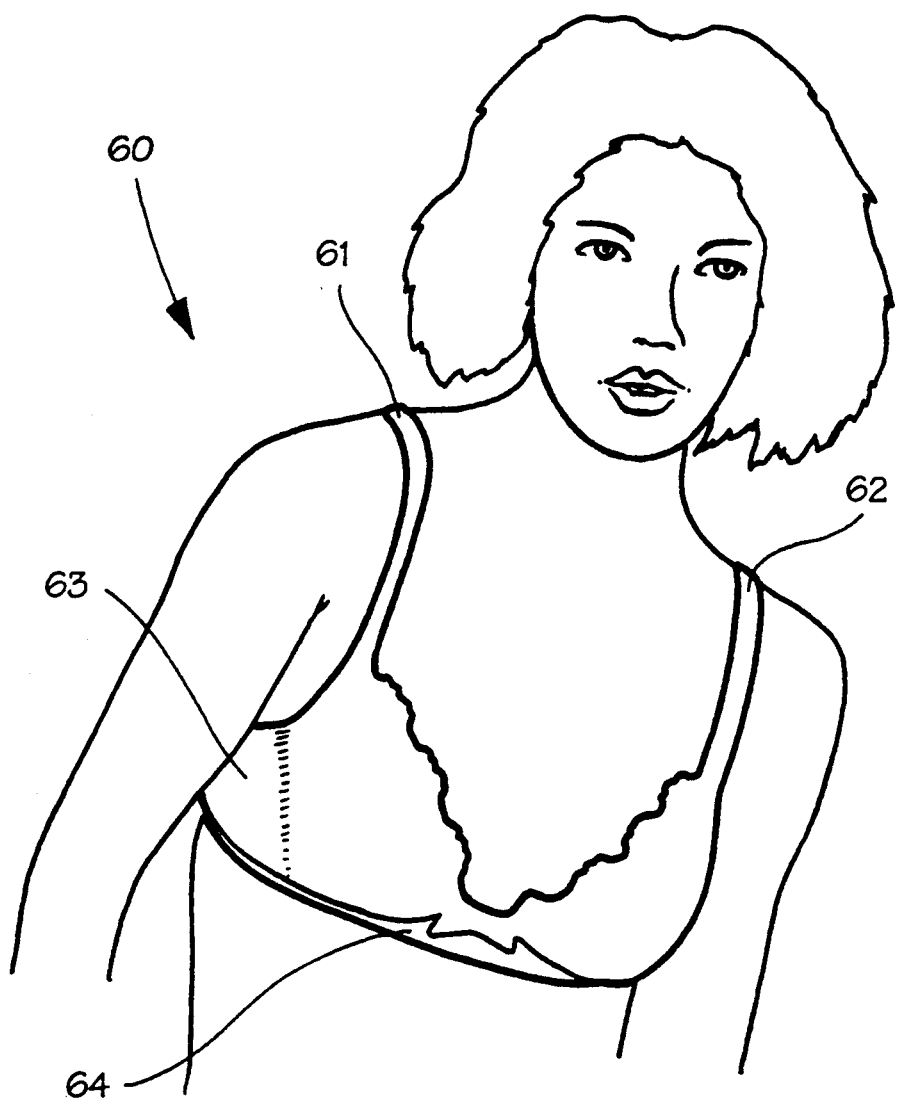
FIG. 14 is a brassiere, including elastic moisture management shoulder straps, back strap and under-cup material according to an embodiment of the present invention.

A brassiere 60 incorporating elastic moisture management fabric according to the invention is shown in FIG. 14. Brassiere 60 includes shoulder straps 61 and 62 formed of a narrow width of the fabric 20. The back strap 63 may also be formed from a wider width of moisture management fabric described in this application. In addition, under-cup elastic panel 64 may be constructed of the same fabric.

Moisture management elastic fabric 20 is described as generally representative of the fabric from which each of these structures are constructed. Moisture management fabric 20 is constructed on a warp knitting machine with weft insertion, such as the Raschelina RD3 warp knitting machine manufactured by Maschinenfabrik Jakob Müller AG, of Frick, Switzerland. Other warp knitting machines with weft insertion may also be used, as can other types of textile forming machines which can form fabrics having obverse faces of different yarns, with laid-in elastic. The actual physical structure of the moisture management elastic fabric is conventional. The novelty of the invention resides in the provision of hydrophobic fibers residing on the skin side of the fabric and hydrophilic fibers residing on the outer side of the fabric to provide an elastic fabric which has moisture management characteristics.

As is shown in FIGS. 6-9, inner moisture transport fabric layer 21 is constructed of hydrophobic yarns formed from polyester fiber, such as fiber sold by DuPont under the trademarks Coolmax or Thermax, or from generic polyester fibers. The yarns which form the fabric layer 21 are intended to reside in skin contact during garment wear, and for this reason as many as three or four separate yarns of relatively low denier are knitted in a bulky knit to provide a soft, comfortable skin-contacting surface. These hydrophobic yarns which form the inner skin-contacting layer 21 quickly capture the moisture on the yarn surfaces and transport the moisture away from the skin through the thickness of the fabric layer 21.

As is shown in FIGS. 10-13, a moisture dispersal fabric layer 22 is constructed of hydrophilic yarns and defines a second fabric face obverse to the fabric layer 21. Fabric layer 22 is intended to reside in spaced-apart relation from the skin during garment wear. The moisture dispersal fabric layer 22 receives moisture from the hydrophobic moisture transport layer 21. The moisture dispersal fabric layer 22 is constructed of hydrophilic yarns formed of fibers such as Hydrofil (r) brand fiber sold by Allied Fibers, or cotton, or blends of polyester and cotton. The fabric layer 22 is integrated with the transport layer 21 at their respective boundaries to receive and disperse moisture transported to it by the inner moisture transport layer 21. While the fabric layers 21 and 22 are distinct, they are integrated with each other and reside in contact with each other so that moisture transported from the hydrophobic transport fabric layer 21 moves into contact with the hydrophilic dispersal fabric layer 22. This results in a "push-pull" effect, whereby body heat "pushes" the moisture away from the skin along the surfaces of the hydrophobic fibers to the point where they are picked up by the fabric layer 22 and "pulled" away from the fabric layer 21 and towards the outer surface of the fabric layer 22. The "pull" results from the evaporation at the outer surface, which causes moisture in the wetter, inner areas of the fabric layer 22 to migrate towards the less wet outer areas.

The transverse diagonal loops formed by the knitting structure run in the warp direction (length) of the fabric, while the yarns running in the weft direction (width) of the fabric 20 are essentially straight. For this reason, the stretch of the fabric 20 is almost all in the warp direction of the fabric. Elastic yarns 23, such as rubber, latex or a long chain polyurethane elastomer such as Lycra brand spandex elastic, are laid-in to the structure of the fabric 20. The elastic yarns 23 run along the length of the fabric 20 and provide controlled resistance to elongating forces on the fabric 20, and quick return of the fabric 20 to its original length when the elongating forces are removed.

Figure 2:
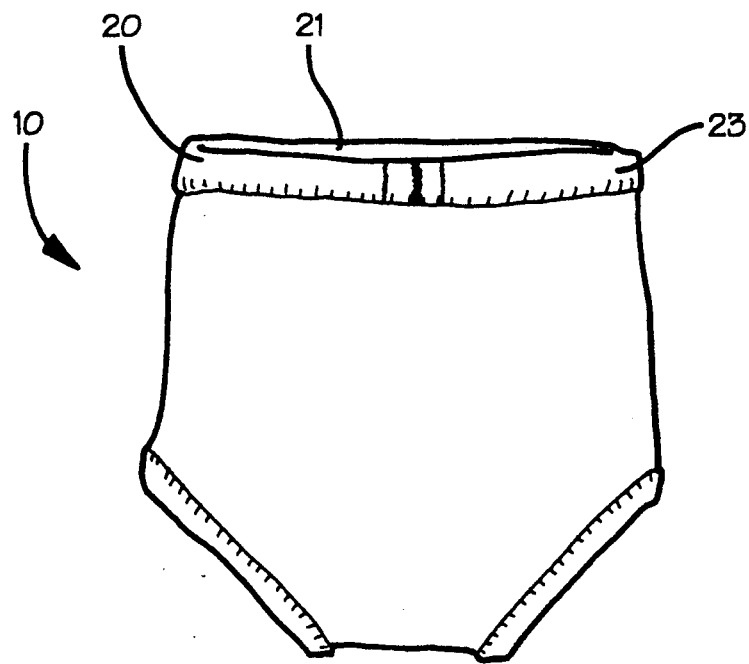
FIG. 2 is a view of the back side of the garment shown in FIG. 1.

Moisture management fabric according to the waistband embodiment shown in FIGS. 1 and 2 is approximately one to one-and-one-half inches wide (2.5 to 4 cm) and has stretch of approximately 100 percent in the warp, or lengthwise, direction.

Moisture management fabric constructed into the headband 30 according to the embodiment shown in FIG. 3 is also approximately one to one-and-one-half inches wide (2.5 to 4 cm) and has stretch of approximately 50 to 100 percent in the warp, or lengthwise, direction.

Moisture management fabric constructed into the wristband 40 according to the embodiment shown in FIG. 4 is also approximately two to three inches wide (5 to 8 cm) and has stretch of approximately 50 to 100 percent in the warp, or lengthwise, direction.

The moisture management fabric, when assembled to form a medical product such as the brace 50 according to the embodiment shown in FIG. 5, is also approximately eight to 10 inches wide (12 to 25 cm) and has stretch of approximately 40 to 80 percent in the warp, or lengthwise, direction.

In each case, the item 30, 40 or 50 is constructed by cutting the fabric to its suitable length and then seaming the two cut ends together with seaming stitches 33, 43, 53, respectively, to form an endless band.

In all of the embodiments disclosed above, the various fabrics can be treated with an anti-bacterial agent to retard odor and bacteria growth. Patterns and designs can also be knitted into the fabric by conventional knitting design techniques, including cross-dyeing and using different colored and textured yarns.

A moisture management elastic fabric and several moisture management garments are described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. A multi-layer moisture management elastic fabric strap of indeterminate length, comprising:
   (a) a moisture transport fabric layer constructed of hydrophobic yarns and defining a first fabric face for residing in skin contact during garment wear and for wicking moisture away from the skin;
   (b) a moisture dispersal fabric layer constructed of hydrophilic yarns and defining a second fabric face for residing in spaced-apart relation from the skin during garment wear and for receiving moisture from the hydrophobic moisture transport layer; and
   (c) elastic yarns integrated with the yarns of the moisture transport fabric layer and the yarns of the moisture dispersal fabric layer to form a single, integrated fabric strap which is highly elastic having stretch of no less than 100 percent in the lengthwise direction with substantially no stretch in the widthwise direction; whereby said fabric strap may be used as a waistband, wristband, headband, or brassiere strap.

2. A moisture management elastic fabric strap according to claim 1, wherein the hydrophobic yarns and the hydrophilic yarns of said elastic fabric strap are warp knitted, and wherein said elastic yarns are laid into the structure of the warp knitted yarns.

3. A moisture management elastic fabric strap according to claim 1, wherein the hydrophobic yarn of the moisture transport layer is chosen from the group consisting of polyester and polypropylene.

4. A moisture management elastic fabric strap according to claim 1, wherein the hydrophilic yarn of the moisture dispersal fabric layer is chosen from the group consisting of hydrophilic nylon, cotton and rayon.

5. A moisture management elastic fabric strap according to claim 1, wherein the elastic yarn is chosen from the group consisting of rubber, latex and a long chain polyurethane elastomer.

6. A moisture management elastic fabric strap according to claim 2, wherein the structure of the warp knitting is a Raschel structure.

7. A moisture management elastic fabric strap according to claim 6, wherein said elastic fabric strap comprises a waistband for a garment.

8. A moisture management elastic fabric strap according to claim 6, wherein said elastic fabric strap comprises a body part support wrap.

9. A moisture management elastic fabric strap according to claim 2 wherein said elastic yarns are laid into the fabric strap intermediate the moisture transport fabric layer and the moisture dispersal fabric layer.

10. A warp-knitted multi-layer moisture management elastic fabric strap of indeterminate length, comprising:
    (a) a moisture transport fabric layer constructed of hydrophobic yarns and defining a knitted first fabric face for residing in skin contact during garment wear and for wicking moisture away from the skin;
    (b) a moisture dispersal fabric layer integrated by knitting with said moisture transport fabric layer, said moisture dispersal fabric layer constructed of hydrophilic yarns and defining a knitted second fabric face obverse to the first fabric face for residing in spaced-apart relation from the skin during garment wear and for receiving moisture from the hydrophobic moisture transport layer; and
    (c) elastic yarns integrated by being laid in with the yarns of the moisture transport fabric layer and the yarns of the moisture dispersal fabric layer to form a single, integrated fabric strap which is highly elastic;
    (d) said elastic fabric strap comprising a narrow-width elastic fabric having stretch of no less than 100 percent in the lengthwise direction and substantially no stretch in the width direction; whereby said fabric strap may be used as a waistband, wristband, headband, or brassiere strap.

11. A moisture management elastic fabric strap according to claim 10, wherein said fabric strap is no less than one inch wide and no more than two inches wide.

12. A moisture management elastic fabric strap, according to claim 11, wherein the hydrophobic yarns and the hydrophilic yarns of said elastic fabric strap are warp knitted, and wherein said elastic yarns are laid into the structure of the warp knitted yarns.

13. A moisture management elastic fabric strap according to claim 11, wherein the hydrophobic yarn of the moisture transport layer is chosen from the group consisting of polyester and polypropylene.

14. A moisture management elastic fabric strap according to claim 11, wherein the hydrophilic yarn of the moisture dispersal fabric layer is chosen from the group consisting of hydrophilic nylon, cotton and rayon.

15. A moisture management elastic fabric strap according to claim 11, wherein the elastic yarn is chosen from the group consisting of rubber, latex and a long chain polyurethane elastomer.

16. A moisture management elastic fabric strap according to claim 11, wherein the structure of the warp knitting is a Raschel structure.

17. A moisture management elastic fabric strap according to claim 11, in combination with a garment.

18. A moisture management elastic fabric strap according to claim 11, the fabric strap is formed into a body wrap.

19. A moisture management elastic fabric strap according to claim 11, the fabric strap is formed strap components of a brassiere.

* * * * *